United States Patent [19]

Hewett et al.

[11] Patent Number: 6,046,133
[45] Date of Patent: Apr. 4, 2000

[54] HERBICIDAL COMPOSITIONS

[75] Inventors: Richard Henry Hewett; Alan Gamblin, both of Ongar, United Kingdom; Bernard Leroux, Research Triangle Park, N.C.; Sylvie Ronssin, Lyons, France

[73] Assignee: Rhone-Poulenc Agriculture Ltd., Ongar, United Kingdom

[21] Appl. No.: 09/091,509

[22] PCT Filed: Dec. 18, 1996

[86] PCT No.: PCT/EP96/05678

§ 371 Date: Oct. 1, 1998

§ 102(e) Date: Oct. 1, 1998

[87] PCT Pub. No.: WO97/23134

PCT Pub. Date: Jul. 3, 1997

[30] Foreign Application Priority Data

Dec. 22, 1995 [GB] United Kingdom ................... 9526436

[51] Int. Cl.[7] .................... A01N 37/34; A01N 33/06; A01N 37/18; A01N 41/10; A01N 43/66
[52] U.S. Cl. .............................. 504/133; 504/141
[58] Field of Search ..................... 504/141, 133

[56] References Cited

U.S. PATENT DOCUMENTS

| | | | |
|---|---|---|---|
| 5,222,595 | 6/1993 | Gouge et al. | 206/205 |
| 5,224,601 | 7/1993 | Gouge et al. | 206/524.7 |
| 5,323,906 | 6/1994 | Gouge et al. | 206/524.7 |
| 5,351,831 | 10/1994 | Gouge et al. | 206/524.7 |
| 5,804,532 | 9/1998 | Cain et al. | 504/309 |

FOREIGN PATENT DOCUMENTS

| | | |
|---|---|---|
| 0213892 | 3/1987 | European Pat. Off. . |
| 0496630 | 7/1992 | European Pat. Off. . |
| 0496631 | 7/1992 | European Pat. Off. . |
| 0625505 | 11/1994 | European Pat. Off. . |
| 0625508 | 11/1994 | European Pat. Off. . |
| 0577702 | 8/1995 | European Pat. Off. . |
| 93/08095 | 4/1993 | WIPO . |

OTHER PUBLICATIONS

The Pesticide Manual, ed. CliveTomlin, 10th edition, British Crop Protection Council, England, pp. 10–11, 14–15, 21–22, 32–33, 51–52, 345–346, 376–378, 693–694, 699–700, 779–780, 842–843, 962–963, and 1025–1026 (1994).

Pallett et al. "Inhibition of 4–Hydroxyphenylpyruvate Dioxygenase: the Mode of Action of the Herbicide RPA 201772 (Isoxaflutole)". Pesticide Science. 50:83–84. 1997. Summary of paper presented on Mar. 13, 1996.

*Primary Examiner*—S. Mark Clardy
*Attorney, Agent, or Firm*—Burns, Doane, Swecker & Mathis, L.L.P.

[57] ABSTRACT

The invention relates to compositions comprising (a) a 2-cyano-1,3-dione derivative or an agriculturally acceptable salt, metal complex or enolic tautomeric form thereof; and (b) at least one member of the group consisting of a triazine herbicide, a chloroacetamide herbicide, a 2,6-dinitroaniline herbicide, aclonifen, which is 2-chloro-6-nitro-3-phenoxyaniline; diuron, which is 3-(3,4-dichlorophenyl)-1, 1-dimethylurea; and a hydroxybenzonitrile herbicide; and to their use as herbicides.

61 Claims, No Drawings

HERBICIDAL COMPOSITIONS

This application has been filed under 35 USC 371 as the national stage of international application PCT/EP96/05678, filed Dec. 18, 1996.

This invention relates to new herbicidally active compositions comprising a 2-cyano-1,3-dione derivative and another herbicide.

European Patent Publication Nos. 0496630, 0496631, 0625505 and 0625508 disclose certain I -phenyl-2-cyano-1,3-dione derivatives possessing herbicidal properties. European Patent Publication No. 0213892 discloses herbicidally active enols. While possessing a good level of herbicidal activity, many of these compounds lack a broad enough spectrum of activity to control certain weeds infesting areas used or to be used for growing crops (for example maize or sugar cane). A number of known herbicides provide control of many weeds infesting crop-growing areas. These include: 1,3,5-triazine and 1,2,4-triazinone herbicides (hereinafter referred to as triazine herbicides) such as ametryn ($N^2$-ethyl-$N^4$-isopropyl-6-methylthio-1,3,5-triazine-2,4-diamine), atrazine (6-chloro-$N^2$-ethyl-$N^4$-isopropyl-1,3,5-triazine-2,4-diamine), terbutryn ($N^2$-tert-butyl-$N^4$-ethyl-6-methylthio-1,3,5-triazine-2,4-diamine) and metribuzin (4-amino-6-tert-butyl-3-methylthio-1,2,4-triazin-5(4H)-one); Chloroacetamides such as alachlor (2-chloro-2',6'-diethyl-N-methoxymethylacetanilide), acetochnor (2-chloro-N-ethoxymethyl-6'-ethylacet-o-toluidide), metolachlor [2-chloro-6'-ethyl-N-(2-methoxy-1-methylethyl)acet-o-toluidide], propachlor (2-chloro-N-isopropylacetanilide) and dimethenamid [2-chloro-N-(2,4-dimethyl-3-thienyl)-N-(2-methoxy-1-methylethyl)acetamide]; 2,6-dinitroaniline herbicides such as pendimethalin [N-(1-ethylpropyl)-3,4-dimethyl-2,6-dinitrobenzenamine] and trifluralin [2,6-dinitro-N,N-dipropyl-4-(trifluoromethyl)benzenamine]; aclonifen (2-chloro-6-nitro-3-phenoxyaniline), diuron [3-(3, 4-dichlorophenyl)-1,1-dimethylurea]; and hydroxybenzonitrile herbicides such as bromoxynil [3,5-dibromo-4-hydroxybenzonitrile] and ioxynil [4-hydroxy-3,5-diiodobenzonitrile], each of which is disclosed in "The Pesticide Manual", 10th edition (British Crop Protection Council), 1994.

As a result of research and experimentation it has been found that the use of one or more of these herbicides, in combination with certain 2-cyano-1,3-dione derivatives, extends the spectrum of herbicidal activity. Therefore the said combinations represents an important technological advance. The term "combination" as used in this specification refers to the "combination" of the 2-cyano-1,3-dione derivative and the partner herbicide.

Surprisingly, in addition to this, it has been found that under certain conditions the combined herbicidal activity of certain 2-cyano-1,3-diones with certain other herbicides for the control of important weed species such as *Setaria viridis, Setaria viridis*, or *Echinochloa crus-galli*, is greater than expected, without an unacceptable increase in crop phytotoxicity, i.e the mixture shows synergism as defined by Limpel, L. E. P. H. Schuldt and D. Lamont, 1962, 1. Proc. NEWCC 16, 48–53, using the formula:

$$E = X + Y - \frac{X \cdot Y}{100}$$

also known as the Colby formula (Colby S. R., 1967, Weeds 15, 20–22), where:

E=the expected percent inhibition of growth by a mixture of two herbicides A and B at defined doses.

X=the percent inhibition of growth by herbicide A at a defined dose.

Y=the percent inhibition of growth by herbicide B at a defined dose.

When the observed percentage of inhibition by the mixture is greater than the expected value E using the formula above the combination is synergistic.

This unexpected synergistic effect gives improved reliability in controlling these competitive weeds of many crop species, and contributes to a considerable reduction in the amount of active ingredient required for weed control.

This remarkable synergistic effect gives improved reliability of control of a number of weed species and allows for a reduction in the amount of active ingredients employed.

A high level of control of these weeds is desirable to prevent:

1) yield loss, through competition and/or difficulties with harvest,
2) crop contamination leading to storage and cleaning difficulties, and
3) unacceptable weed seed return to the soil.

According to the present invention there is provided a method of controlling the growth of weeds at a locus which comprises applying to the locus a herbicidally effective amount of:

(a) a 2-cyano-1,3-dione herbicide, or an agriculturally acceptable salt, metal complex or enolic tautomeric form thereof; and (b) at least one member of the group consisting of a triazine herbicide, a chloroacetamide herbicide, a 2,6-dinitroaniline herbicide, aclonifen, diuron, and a hydroxybenzonitrile herbicide.

For this purpose, the 2-cyano-1,3-dione and partner herbicide are normally used in the form of herbicidal compositions (i.e. in association with a herbicidally acceptable diluent or carrier and/or surface active agent), for example as hereinafter described. In this description it will be understood that the term "partner herbicide" means at least one member of the group consisting of a triazine herbicide, a chloroacetamide herbicide, a 2,6-dinitroaniline herbicide, aclonifen, diuron, and a hydroxybenzonitrile herbicide.

Preferably the 2-cyano-1,3-dione derivative has the formula (I):

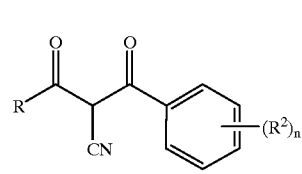

(I)

wherein $R^1$ is $C_{1-6}$ alkyl or $C_{3-6}$ cycloalkyl optionally bearing $C_{1-6}$ alkyl;

$R^2$ is selected from halogen, —$S(O)_p$Me and $C_{1-6}$ alkyl or haloalkyl, n is two or three; and p is zero, one or two.

Compounds of formula I above may exist in enolic tautomeric forms that may give rise to geometric isomers around the enolic double bond. Furthermore, in certain cases the groups $R^1$ and $R^2$ may give rise to stereoisomers and geometric isomers. All such forms are embraced by the present invention.

By the term "agriculturally acceptable salts" is meant salts the cations or anions of which are known and accepted in the art for the formation of salts for agricultural or horticultural use. Preferably the salts are water-soluble. Suitable salts with bases include alkali metal (eg. sodium and potassium), alkaline earth metal (eg. calcium and magnesium), ammonium and amine (eg. diethanolamine, triethanolamine, octylamine, morpholine and dioctylmethylamine) salts. Suitable acid addition salts, formed by compounds of formula (I) containing an amino group, include salts with inorganic acids, for example hydrochlorides, sulphates, phosphates and nitrates and salts with organic acids, for example acetic acid.

By the term "metal complexes" is meant compounds in which one or both of the oxygen atoms of the 1,3-dione act as chelating agents to a metal cation. Examples of such cations include zinc, manganese, cupric, cuprous, ferric, ferrous, titanium and aluminium. It will be understood that in the description that follows, reference to 2-cyano-1,3-diones includes agriculturally acceptable salts, metal complexes or enolic tautomeric forms thereof.

In formula (I) above, compounds preferably $R^1$ is 1-methylcyclopropyl or, more preferably cyclopropyl.

In formula (I) above, compounds in which n is three and the groups $(R^2)_n$ occupy the 2,3 and 4-positions of the benzoyl ring; or in which n is two and the groups $(R^2)_n$ occupy the 2 and 4- positions of the benzoyl ring are preferred.

In formula (I) above, $R^2$ is preferably selected from halogen (preferably chlorine or bromine), —S(O)$_p$Me and trifluoromethyl.

In formula (I) above, preferably one of the groups $R^2$ is —S(O)$_p$Me.

The most preferred compound of formula (I) above is 2-cyano-3-cyclopropyl-1-(2-methylsulphonyl-4-trifluoromethylphenyl)propan-1,3-dione, hereafter referred to as compound A.

Preferably the triazine herbicide is a compound of formula II:

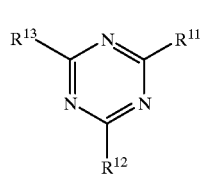

(II)

wherein $R^{11}$ represents chlorine or straight- or branched chain alkylthio or alkoxy having from one to six carbon atoms; $R^{12}$ represents azido, monoalkylamino, dialkylamino or cycloalkylamino, in which the alkyl or cycloalkyl moieties may be optionally substituted by one or more substituents selected from cyano and alkoxy; and $R^{13}$ represents straight- or branched-chain N-alkylamino having from one to six carbon atoms; or of formula IIa.

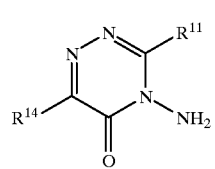

(IIa)

wherein $R^{14}$ represents straight- or branched chain alkyl having from one to six carbon atoms.

Preferred compounds of formula II above are those in which $R^{11}$ represents chlorine, $R^{13}$ represents N-ethylamino and $R^{12}$ represents N-ethylamino, N-(2-methylpropanenitrile)amino or N-isopropylamino, known respectively as simazine, cyanazine and atrazine, with atrazine being most preferred. Another preferred compound of formula (II) above is the compound wherein $R^{11}$ is methylthio, $R^{12}$ is N-isopropylamino, and $R^{13}$ is N-ethylamino, which is ametryn. The use of ametryn is particularly preferred when the method is used at a locus use, or to be used for the growing of sugar-cane.

A preferred compound of formula IIa above is the compound in which $R^{11}$ represents methylthio, $R^{14}$ represents tert-butyl, which is known as metribuzin.

Preferably the chloroacetamide herbicide is of formula (III):

$$Ar-N(R^{31})COCH_2Cl \qquad (III)$$

wherein $R^{31}$ represents hydrogen, $C_{1-6}$ alkyl, haloalkyl, alkoxy or alkoxyalkyl; alkenyl, haloalkenyl, alkynyl, haloalkynyl or acylamidoalkyl having up to six carbon atoms;

Ar represents thienyl or phenyl optionally substituted by one or more groups selected from the group consisting of halogen, amino, $C_{1-6}$ alkyl, haloalkyl, alkoxy and alkoxyalkyl.

The group $R^{31}$ can give rise to optical and/or stereoisomers, and it will be understood that both racemic and enantiomeric forms of this compound are included in this definition.

Compounds of formula (III) above in which Ar represents phenyl or thienyl optionally substituted by one or preferably two groups which may be the same or different selected from ethyl and methyl are also preferred.

A preferred compound of formula (III) is the compound wherein $R^{31}$ represents methoxymethyl and Ar represents 2,6-diethylphenyl, which is known as alachlor.

Another preferred compound of formula (III) is the compound wherein $R^{31}$ represents ethoxymethyl and Ar represents 2-ethyl-6-methylphenyl, which is known as acetochlor.

Another preferred compound of formula (III) is the compound wherein $R^{31}$ represents 2-methoxy-1-methylethyl and Ar represents 2-ethyl-6-methylphenyl, which is known as metolachlor. Both the racemic form of metolachlor and the partially resolved form, known as alpha-metolachor, and mixtures thereof, are preferred.

Another preferred compound of formula (III) is the compound wherein $R^{31}$ represents 1-methylethyl and Ar represents phenyl, which is known as propachlor.

Another preferred compound of formula (III) is the compound wherein $R^{31}$ represents 2-methoxy-1-methylethyl and Ar represents 3-(2,4-dimethyl)thienyl, which is known as dimethenamid. Both the racemic form of dimethenamid and the partially resolved (S-) form, known as S-dimethenamid, and mixtures thereof, are preferred.

Preferably the 2,6-dinitroaniline herbicide is a compound of the formula IV:

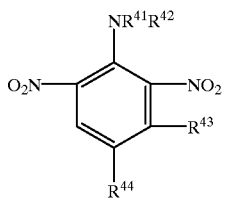
(IV)

wherein:

$R^{41}$ represents:

straight or branched chain alkyl or alkenyl having up to 12 carbon atoms which may be substituted by one or more halogen atoms or cycloalkyl groups;

$R^{42}$ represents hydrogen or a group $R^{41}$ as defined above, $R^{41}$ and $R^{42}$ being the same or different;

$R^{43}$ represents:

hydrogen or halogen;

straight or branched chain alkyl having from 1 to 12 carbon atoms which may be substituted by one or more halogen atoms; or an unsubstituted amino group;

$R^{44}$ represents:

halogen;

straight or branched chain alkyl having from 1 to 12 carbon atoms which may be substituted by one or more halogen atoms;

straight or branched chain alkylsulphonyl having from 1 to 12 carbon atoms which may be substituted by one or more halogen atoms;

or sulphamoyl.

Preferred compounds of formula (IV) include those wherein $R^{41}$ is selected from the group consisting of ethyl, propyl, butyl, 1-ethylpropyl, 2-methyl-1-propenyl, cyclopropylmethyl and 2-chloroethyl.

Preferred compounds of formula (IV) include those wherein $R^{42}$ is selected from hydrogen, ethyl and propyl.

Preferred compounds of formula (IV) include those wherein $R^{43}$ is selected from hydrogen, methyl and unsubstituted amino.

Preferred compounds of formula (IV) include those wherein $R^{44}$ is selected from methyl, tert-butyl, isopropyl and trifluoromethyl.

Especially preferred compounds of formula (IV) are:

2,6-dinitro-N,N-dipropyl-4-(trifluoromethyl) benzeneamine and

N-(1-ethylpropyl)-3,4-dimethyl-2,6-dinitrobenzeneamine, which are known respectively as trifluralin and pendimethalin, pendimethalin being most preferred.

The hydroxybenzonitrile herbicide is preferably bromoxynil or ioxynil in the form of the parent phenol (acid equivalent: a.e.), an agriculturally acceptable salt or ester thereof, preferably an agriculturally acceptable metal or amine salt, or an agriculturally acceptable ester thereof with an alkanoic acid containing from 2 to 10 carbon atoms, or a mixture thereof. In particular, the butyrate, octanoate and heptanoate esters, or mixtures thereof, are preferred, with the octanoate ester most preferred.

The amounts of 2-cyano-1,3-dione and other herbicide applied vary depending on the weeds present and their population, the compositions used, the timing of the application, the climatic and edaphic conditions, and (when used to control the growth of weeds in crop growing areas) the crop to be treated. In general, taking these factors into account, the dose rates given below are used. However, it will be understood that higher or lower application rates may be used, depending upon the problem of weed control encountered. When applied to a crop-growing area, the rate of application should be sufficient to control the growth of weeds without causing substantial permanent damage to the crop.

The method described above may be used to control a very wide spectrum of annual broad-leafed weeds and grass weeds in crops, e.g. maize or sugar-cane, without significant permanent damage to the crop. The combined use described above offers both foliar and residual activity and consequently can be employed over a long period of crop development, i.e. from pre-weed pre-crop emergence to post-weed post-crop emergence. In the method according to this feature of the present invention the combined use of (a) and (b) to control grass weeds in maize or sugarcane is preferred. Where (b) is a member of the group consisting of a chloroacetamide herbicide, a 2,6-dinitroaniline herbicide, aclonifen and a hydroxybenzonitrile herbicide, the method is preferably used to control grass weeds in maize. Where (b) is diuron the method is preferably used to control grass weeds in sugarcane. Where the partner herbicide is a member of the group consisting of a triazine herbicide, a chloroacetamide herbicide, a 2,6-dinitroaniline herbicide, aclonifen and diuron, the herbicides are generally applied pre-emergence of the weeds (for example by surface application and in particular pre-plant incorporated) and may be applied after planting of a crop (where present); or early post emergence of the weeds and crops. Most preferably, these herbicides are applied in combination with (a) after planting of a crop and pre-emergence of the weeds, or pre-plant incorporated. Where the partner herbicide is a hydroxybenzonitrile herbicide, the combination with (a) is generally applied post-emergence of the weeds, more preferably early-post emergence.

In accordance with the usual practice (and a preferred method according to the present invention) a tank mix may be prepared prior to use by combining separate formulations of the individual herbicidal components.

Where the partner herbicide is a triazine herbicide, application rates from 5 g to 500 g of 2-cyano-1,3-dione and from 250 g to 5000 g of the triazine herbicide per hectare generally give good results. For the selective control of weeds at a locus of weed infestation which is an area used, or to be used, for growing of crops application rates from 5 g to 500 g of 2-cyano-1,3-dione and from 250 g to 5000 g of the triazine herbicide per hectare are particularly suitable, preferably from 25 to 200 g of 2-cyano-1,3-dione and from 500 g to 1500 g of the triazine herbicide per hectare.

Where the triazine herbicide is ametryn it is preferably used in combination with a 2-cyano-1,3-dione at a dose rate of from 250 to 4000 grammes per hectare of ametryn, more preferably from 500 to 2000 g per hectare.

Where the partner herbicide is a chloroacetamide herbicide, application rates from 0.5 g to 512 g of 2-cyano-1,3-dione and from 8 to 4000 g of the chloroacetamide herbicide per hectare generally give good results. For the selective control of weeds at a locus of weed infestation which is an area used, or to be used, for growing of crops application rates from 0.5 g to 512 g of 2-cyano-1,3-dione and from 20 to 4000 g of the chloroacetamide herbicide per hectare are particularly suitable, preferably from 20 to 200 g of 2-cyano-1,3-dione and from 200 to 3000 g of the chloroacetamide herbicide per hectare, even more preferably from 25 to 150 g of 2-cyano-1,3-dione and from 350 to 2000 g (especially from 450 g to 2000 g) of the chloroacetamide herbicide per hectare.

Where the partner herbicide is a 2,6-dinitroaniline herbicide, application rates from 0.5 g to 512 g of 2-cyano-1,3-diones and from 8 g to 3000 g of the 2,6-dinitroaniline herbicide per hectare generally give good results. For the selective control of weeds at a locus of weed infestation which is an area used, or to be used, for growing of crops application rates of from 5 g to 512 g of 2-cyano-1,3-dione and from 8 g to 3000 g of the 2,6-dinitro aniline herbicide per hectare are particularly suitable, preferably from 20 g to 200 g of 2-cyano-1,3-dione and from 150 g to 2000 g of the 2,6-dinitroaniline herbicide per hectare, most preferably from 25 g to 150 g of 2-cyano-1,3-diones and from 250g to 1000 g of the 2,6-dinitroaniline herbicide per hectare.

Where the partner herbicide is aclonifen, application rates from 1 g to 500 g of the 2-cyano-1,3-dione and from 30 g to 2500 g of aclonifen per hectare give good results, more preferably from 10 g to 200 g of the 2-cyano-1,3-dione and from 500 g to 1000 g of aclonifen per hectare.

Where the partner herbicide is diuron, application rates 0.5 g to 500 g of the 2-cyano-1,3-dione and from 100 g to 3000 g of diuron per hectare give good results, more preferably from 25 g to 150 g of the 2-cyano-1,3-dione and from 500 g to 2000 g of diuron per hectare.

Where the partner herbicide is a hydroxybenzonitrile (HBN) herbicide, application rates of from 5 g to 500 g of the 2-cyano-1,3-dione and from 30 g to 600 g acid equivalent (a.e.) of HBN herbicide per hectare give good results, more preferably from 20 to 300 g of the 2-cyano-1,3-dione and from 60 g to 200 g a.e. of HBN herbicide per hectare.

The method of the invention is most preferably used for the control of weeds at a locus used, or to be used for the growing of a crop. When applied to a crop-growing area, the rate of application should be sufficient to control the growth of weeds without causing substantial permanent damage to the crop. The dose rate of the combination used should generally provide a sufficiently persistent level of activity to control weeds for some time after application to the locus. Preferably the treatment should be persistent for 45 to 60 days after application.

The mixtures of the present invention may also be used to control the growth of weeds at loci which are not crop-growing areas but in which the control of weeds is nevertheless desirable. Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

The following non-limiting examples illustrate the invention. In the description that follows the following trade marks appear: Lasso, Frontiere, Duelor, Harness Plus, Prowl, Propixine, Buctril. The abbreviation 'a.i.' means active ingredient. Also, certain weeds and crops are indicated by their Bayer codes.

EXAMPLE 1

Seeds of *Setaria faberi*, *Setaria viridis* or *Echinochloa crus-galli* were sown in non-sterilised clay loam soil in seven centimeter by seven centimeter plastic plant pots. The pots were watered and allowed to drain. The soil surface was then sprayed with a range of concentrations of either Compound A, pendimethalin, metolachlor, acetochlor, aclonifen, atrazine or diuron alone, or mixtures of Compound A with each of these herbicides, dissolved in 50/50 weight/weight of acetone/water. In all cases technical material was used. The solutions were sprayed using a track sprayer which delivered the equivalent of 290 liters/ha 43 centimeters above the soil surface. Four replicates were performed, and the treated plots were placed at random and held in a glasshouse, standing on moist capillary matting under lights, with watering overhead three times daily.

Two weeks after treatment the percent reduction in plant growth was assessed in comparison with an untreated control, and the mean result for each application rate assessed. The Colby formula was applied to the results to determine the nature of the interaction between the mixtures of herbicides. In the Tables that follow the figures shown in parentheses represent the expected reduction in growth by the mixtures of herbicides according to the Colby formula.

Results:

TABLE 1

Compound A and pendimethalin against *Setaria faberi*

| | Dose | | Pendimethalin | | |
|---|---|---|---|---|---|
| | (g/ha) | 0 | 8 | 16 | 32 |
| | 0 | — | 0.0 | 7.5 | 57.5 |
| Cpd A | 8 | 32.5 | 73.8 (32.5) | 57.5 (37.6) | 86.3 (71.3) |
| | 16 | 68.8 | 82.5 (68.8) | 82.5 (71.1) | 93.8 (86.7) |

TABLE 2

Compound A and pendimethalin against *Echinochloa crus-galli*

| | Dose | | Pendimethalin | | | |
|---|---|---|---|---|---|---|
| | (g/ha) | 0 | 8 | 16 | 32 | 64 |
| | 0 | — | 0.0 | 38 | 0.0 | 16.3 |
| Cpd A | 8 | 10.0 | 40.0(10.0) | 58.8(13.4) | 53.8(10.0) | 55.0(24.7) |

TABLE 3

Compound A and metolachlor against *Setaria viridis*

| | Dose | | Metolachlor | | |
|---|---|---|---|---|---|
| | (g/ha) | 0 | 4 | 8 | 16 |
| | 0 | — | 18.8 | 27.5 | 60.0 |
| Cpd A | 16 | 25 | 46.3 (39.1) | 61.3 (45.6) | 77.5 (70.0) |

TABLE 4

Compound A and acetochlor against *Setaria viridis*

| | Dose | | Acetochlor | | |
|---|---|---|---|---|---|
| | (g/ha) | 0 | 3.75 | 15 | 30 |
| | 0 | — | 0.0 | 33.8 | 80.0 |
| Cpd A | 16 | 25 | 50.0 (25.0) | 60.0 (40.0) | 91.3 (81.3) |

TABLE 5

Compound A and aclonifen against *Echinochloa crus-galli*

| Dose | | Aclonifen | | |
|---|---|---|---|---|
| (g/ha) | 0 | 31 | 62 | 124 |
| | 0 | — | 0.0 | 5.0 | 0.0 |
| Cpd A | 8 | 41.3 | 40.0 (41.3) | 56.3 (44.2) | 63.8 (41.3) |
| | 16 | 57.5 | 77.5 (57.5) | 96.3 (59.6) | 73.8 (57.5) |

TABLE 6

Compound A and atrazine against *Echinochloa crus-galli*

| Dose | | Atrazine | | | |
|---|---|---|---|---|---|
| (g/ha) | 0 | 31 | 62 | 124 | 250 |
| | 0 | — | 7.5 | 17.5 | 61.3 | 77.5 |
| Cpd A | 8 | 41.3 | 31.3(45.7) | 67.5(51.6) | 88.8(77.3) | 96.3(86.6) |
| | 16 | 57.5 | 73.8(60.7) | 97.5(64.9) | 95.0(83.6) | 98.8(90.4) |
| | 32 | 91.3 | 98.8(92.0) | 100(92.8) | 100(96.6) | 100(98.0) |

TABLE 7

Compound A and diuron against *Echinochloa crus-galli*

| Dose | | Diuron | | | |
|---|---|---|---|---|---|
| (g/ha) | 0 | 62 | 125 | 250 | 500 |
| | 0 | — | 10.0 | 15.0 | 77.5 | 93.8 |
| Cpd A | 8 | 41.3 | 50.0(47.2) | 85.0(50.1) | 92.5(86.8) | 100(96.4) |

TABLE 7-continued

Compound A and diuron against *Echinochloa crus-galli*

| Dose | | Diuron | | | |
|---|---|---|---|---|---|
| (g/ha) | 0 | 62 | 125 | 250 | 500 |
| 16 | 57.5 | 83.8(61.8) | 81.3(63.9) | 97.5(90.4) | 96.3(97.4) |
| 32 | 91.3 | 96.3(92.2) | 98.8(92.6) | 100(98.8) | 100(99.5) |

EXAMPLE 2

The following field trials were conducted using Compound A (formulated as a wettable powder containing 50% by weight a.i.) with various partner herbicides pre-emergence of the crop and weeds. The trials were conducted at Raymondville, USA (a clay-loam soil; referred to hereafter as 'Location US1') and at Pretoria, South Africa (a clay-loam soil; referred to hereafter as 'Location ZA1') using Compound A alone and in combination with alachlor (as the commercial formulation "Lasso", an emulsifiable concentrate containing 480 g/l a.i.), dimethenamid (as the commercial formulation "Frontiere", an emulsifiable concentrate containing 900 g/l a.i.), metolachlor (as the commercial formulation "Duelor", an emulsifiable concentrate containing 960 g/l a.i.), pendimethalin (as the commercial formulation "Prowl", a suspension concentrate containing 400 g/l a.i.), atrazine (as the commercial formulation "Propixine", a suspension concentrate containing 500 g/l a.i.), and acetochlor (as the commercial formulation "Harness Plus", an emulsifiable concentrate containing 840 g/l a.i). Each of the partner herbicides was also sprayed alone. Two replicates were performed. 34 days after treatment (at US1) or 52 days after treatment (at ZA1) the percentage phytotoxicity was assessed in comparison with an untreated control. The following results were obtained:

TABLE 8

Results from Location US1 (pre-emergence, 34DAT)

| Active ingredient (g/ha) | | | | | Weed species | | | | | | | | Crop |
|---|---|---|---|---|---|---|---|---|---|---|---|---|---|
| Cpd A | Alachlor | Pendimeth-alin | Dimethe-namid | | SETVI | SEFFA | PANMI | DIGSA | SETLU | AMARE | ABUTH | DATST | ZEAMX |
| 12.5 | | | | | 0 | 3 | 0 | 0 | 0 | 0 | 0 | 0 | 0 |
| | 500 | | | | 90 | 90 | 67 | 97 | 99 | 98 | 30 | 17 | 0 |
| 12.5 | 500 | | | | 98 | 96 | 93 | 100 | 100 | 93 | 70 | 65 | 0 |
| | | | | Colby | 90 | 90 | 67 | 97 | 99 | 98 | 30 | 17 | 0 |
| | | 375 | | | 100 | 99 | 94 | 100 | 100 | 98 | 47 | 50 | 0 |
| 12.5 | | 375 | | | 100 | 99 | 98 | 100 | 100 | 99 | 60 | 60 | 0 |
| | | | | Colby | 100 | 99 | 94 | 100 | 100 | 98 | 47 | 50 | 0 |
| | | | 180 | | 99 | 95 | 83 | 99 | 98 | 73 | 63 | 65 | 0 |
| 12.5 | | | 180 | | 68 | 77 | 74 | 88 | 90 | 92 | 65 | 83 | 0 |
| | | | | Colby | 99 | 95 | 83 | 99 | 98 | 73 | 63 | 65 | 0 |

TABLE 9

Results form Location ZA1 (pre-emergence, 52DAT)

| Active ingredient (g/ha) | | | | Weed species | | | | | | | | | |
|---|---|---|---|---|---|---|---|---|---|---|---|---|---|
| Cpd A | Aceto-chlor | Atrazine | Metola-chlor | AMACH | BIDPI | DATST | DIGSA | EPHHL | HITBR | PANMA | SCKPI | SETIT | XANST |
| 12.5 | | | | 92 | 48 | 13 | 77 | 35 | 72 | 82 | 47 | 57 | 7 |
| | 375 | | | 27 | 0 | 12 | 87 | 0 | 0 | 90 | 3 | 88 | 3 |
| 12.5 | 375 | | | 97 | 88 | 47 | 100 | 78 | 82 | 93 | 92 | 100 | 18 |
| | | | Colby | 94 | 48 | 23 | 97 | 35 | 72 | 98 | 49 | 95 | 10 |
| | | 375 | | 90 | 67 | 27 | 28 | 18 | 57 | 23 | 73 | 22 | 13 |
| 12.5 | | 375 | | 97 | 95 | 45 | 83 | 78 | 95 | 88 | 93 | 63 | 33 |
| | | | Colby | 99 | 83 | 36 | 83 | 47 | 88 | 86 | 86 | 66 | 19 |
| | | | 375 | 10 | 0 | 0 | 87 | 0 | 0 | 83 | 2 | 68 | 0 |
| 12.5 | | | 375 | 93 | 78 | 22 | 98 | 77 | 87 | 90 | 63 | 90 | 27 |
| | | | Colby | 93 | 48 | 13 | 97 | 35 | 72 | 97 | 48 | 86 | 7 |

EXAMPLE 3

The following field trials was conducted at Location US1 and at Waverley, USA (silt-loam soil, hereafter referred to as 'Location US2') using Compound A (as used in Example 2 above) either alone or in tank mix combination with bromoxynil (octanoate ester, using the commercial formulation "Buctril 2EC", an emulsifiable concentrate containing 240g/l a.i.) which was also sprayed alone. The compounds were applied early-post emergence to spring-sown weeds found in spring crops. The percentage phytotoxicity was assessed by comparison with an untreated control 34 days after treatment (DAT) at US2 and 37 DAT at US1. Two replicates were performed. The results shown in Tables 10 and 11 were obtained. In these Tables the figures in parentheses indicate the expected level of weed control according to the Colby formula. "Brom" means bromoxynil.

Results

TABLE 10

Results from Location US2 (early post-emergence, 34DAT)

| a.i. | dose (g/ha) | AMARE | ABUTH | ECHCG | ZEAMX (crop) |
|---|---|---|---|---|---|
| Cpd A | 10 | 0 | 0 | 0 | 0 |
| Cpd A | 20 | 0 | 20 | 0 | 0 |
| Brom | 60 | 40 | 0 | 0 | 0 |
| Brom | 120 | 0 | 78 | 0 | 0 |
| Cpd A + Brom | 10 + 60 | 20(40) | 70(0) | 25(0) | 0 |
| Cpd A + Brom | 10 + 120 | 10(0) | 95(78) | 0(0) | 0 |
| Cpd A + Brom | 20 + 60 | 45(40) | 78(20) | 94(0) | 0 |
| Cpd A + Brom | 20 + 120 | 20(0) | 99(82) | 99(0) | 0 |

TABLE 11

Results from Location US2 (early post-emergence, 37DAT)

| a.i. | dose (g/ha) | AMARE | ABUTH | CHEAL | AMATA | ECHCG | HELAN |
|---|---|---|---|---|---|---|---|
| Cpd A | 20 | 0 | 0 | 0 | 0 | 0 | 0 |
| Brom | 120 | 45 | 60 | 94 | 72 | 0 | 85 |
| Cpd A + Brom | 20 + 120 | 83(45) | 65(60) | 100(94) | 98(72) | 20(0) | 100(85) |

According to a further feature of the present invention, there are provided herbicidal compositions comprising:

(a) a 2-cyano-1,3-dione derivative defined above or an agriculturally acceptable salt, metal complex or enolic tautomeric form thereof; and
(b) at least one member of the group consisting of a triazine herbicide, a chloroacetamide herbicide, a 2,6-dinitroaniline herbicide, aclonifen, diuron, and a hydroxybenzonitrile herbicide;

in association with, and preferably homogeneously dispersed in, one or more compatible herbicidally-acceptable diluents or carriers and/or surface-active agents (i.e. diluents or carriers or surface-active agents of the type generally acceptable in the art as being suitable for use in herbicidal compositions and which are compatible with the 2-cyano-1,3-dione derivative and the other herbicide). The term "homogeneously dispersed" is used to include compositions in which combination of herbicides are dissolved in the other components. The term "herbicidal composition" is used in a broad sense to include not only compositions which are ready for use as herbicides but also concentrates which must be diluted before use.

Preferably, the compositions contain from 0.05 to 90% by weight of 2-cyano-1,3-dione derivative(s) and partner herbicide.

The herbicidal compositions may contain both a diluent or carrier and a surface-active (e.g. wetting, dispersing, or emulsifying) agent. Surface-active agents which may be present in herbicidal compositions of the present invention may be of the ionic or non-ionic types, for example sulphoricinoleates, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts or sulphuric acid esters and sulphonic acids such as dinonyl- and dioctyl-sodium sulphono-succinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, absorbent carbon black and clays such as kaolin and bentonite. The solid compositions (which may take the form of dusts, granules or wettable powders) are preferably prepared by grinding the 2-cyano-1,3-dione derivative and partner herbicide with solid diluents or by impregnating the solid diluents or carriers with solutions of 2-cyano-1,3-dione derivative and partner herbicide in volatile solvents, evaporating the solvents and, if necessary, grinding the products so as to obtain powders. Granular formulations may be prepared by absorbing the 2-cyano-1,3-dione derivative and partner herbicide (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agents (for example of the types described above), which may also, when solid, serve as diluents or carriers.

Liquid compositions according to the invention may take the form of aqueous-organic solutions, suspensions and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers.

Wettable powders and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of the 2-cyano-1,3-dione derivative and partner herbicide may be used in the form of self-emulsifying concentrates containing the active substances dissolved in the emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are in the form of aqueous suspension concentrates; wettable powders; water dispersible granules; liquid water soluble concentrates; liquid emulsifiable suspension concentrates; granules or emulsifiable concentrates.

In addition the compositions may be provided in the form of a gel. This is particularly useful where the composition is intended for packaging in a water soluble bag for example as described in European Patent Publication Nos. 0577702 and 0608340, and U.S. Pat. Nos. 5,222,595; 5,224,601; 5,351,831; and 5,323,906.

The processes described in European Patent Publication Nos. 0496630, 0496631, 0625505, and 0625508 may be used to prepare the herbicidal 2-cyano-1,3-dione derivatives.

Herbicidal compositions according to the present invention may also comprise the 2-cyano-1,3-dione derivative and partner herbicide in association with, and preferably homogeneously dispersed in, one or more other pesticidally active compounds and, if desired, one or more compatible pesticidally acceptable diluents or carriers, surface-active agents or conventional adjuvants as hereinbefore described. Preferred partners with the combination of the present invention include one or more other members of the group consisting of triazine herbicides (e.g. atrazine, metribuzin or cyanazine), chloroacetamide herbicides (e.g. alachlor, metolachlor, acetochlor or dimethenamid), 2,6-dinitroaniline herbicides (e.g. pendimethalin or trifluralin), aclonifen and diuron. Also, combinations may be used including other classes of herbicide such as sulfonyl ureas, imidazolinones, thiazoles, ureas and aromatic and heterocyclic di- and tri-ketones etc.

According to a further feature of the present invention, there is provided a product comprising:

(a) a 2-cyano-1,3-dione derivative as defined above or an agriculturally acceptable salt, metal complex or enolic tautomeric form thereof; and (b) at least one member of the group consisting of a triazine herbicide, a chloroacetamide herbicide, a 2,6-dinitroaniline herbicide, aclonifen, diuron and a hydroxybenzonitrile herbicide.

as a combined preparation for simultaneous, separate or sequential use, for example, in controlling the growth of weeds at a locus (e.g. a crop locus).

What is claimed is:

1. A composition comprising a synergistic herbicidally effective amount of:

(a) 2-cyano-3-cyclopropyl-1-(2-methylsulphonyl-4-trifluoromethylphenyl)propan-1,3-dione, or an agriculturally acceptable salt, metal complex or enolic tautomeric form thereof; and (b) at least one member selected from the group consisting of a triazine herbicide, a chloroacetamide herbicide, a 2,6-dinitroaniline herbicide, aclonifen, which is 2-chloro-6-nitro-3-phenoxyaniline; diuron, which is 3-(3,4-dichlorophenyl)-1,1-dimethylurea; and a hydroxybenzonitrile herbicide.

2. The composition according to claim 1 in which (b) is a triazine herbicide.

3. The composition according to claim 2 in which the triazine herbicide is a compound of formula II:

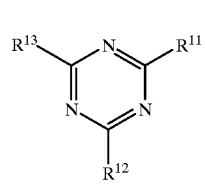

(II)

wherein $R^{11}$ represents chlorine or straight- or branched chain alkylthio or alkoxy having from one to six carbon atoms; $R^{12}$ represents azido, monoalkylamino, dialkylamino or cycloalkylamino, in which the alkyl or cycloalkyl moieties are optionally substituted by one or more substituents selected from the group consisting of cyano and alkoxy; and $R^{13}$ represents straight- or branched-chain N-alkylamino having from one to six carbon atoms;

or of formula IIa:

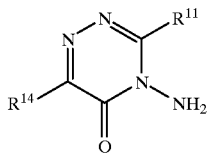

(IIa)

wherein $R^{14}$ represents straight- or branched chain alkyl having from one to six carbon atoms.

4. The composition according to claim 3 in which the triazine herbicide is atrazine, which is (6-chloro-$N^2$-ethyl-$N^4$-isopropyl-1,3,5-triazine-2,4-diamine), or metribuzin, which is (4-amino-6-tert-butyl-3-methylthio-1,2,4-triazin-5 (4H)-one).

5. The composition according to claim 1 in which (b) is a chloroacetamide herbicide.

6. The composition according to claim 5 in which the chloroacetamide herbicide is of formula (III)

wherein $R^{31}$ represents hydrogen, $C_{1-6}$ alkyl, haloalkyl, alkoxy or alkoxyalkyl; alkenyl, haloalkenyl, alkynyl, haloalkynyl or acylamidoalkyl having up to six carbon atoms; and Ar represents thienyl or phenyl optionally substituted by one or more members selected from the group consisting of halogen, amino, $C_{1-6}$ alkyl, haloalkyl, alkoxy and alkoxyalkyl.

7. The composition according to claim 6 in which the chloroacetamide herbicide is acetochlor, which is 2-chloro-N-ethoxymethyl-6'-ethylacet-o-toluidide; or metolachlor, which is 2-chloro-6'-ethyl-N-(2-methoxy-1-methylethyl) acet-o-toluidide or an isomeric mixture thereof.

8. The composition according to claim 1 in which (b) is a 2,6-dinitroaniline herbicide.

9. The composition according to claim 8 in which the 2,6-dinitroaniline herbicide is a compound of the formula IV:

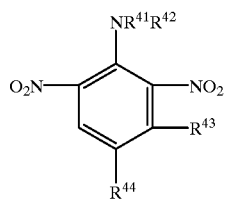

(IV)

wherein:

$R^{41}$ represents:

straight or branched chain alkyl or alkenyl having up to 12 carbon atoms which is unsubstituted or substituted by one or more halogen atoms or cycloalkyl groups;

$R^{42}$ represents hydrogen or a group $R^{41}$ as defined above, $R^{41}$ and $R^{42}$ being the same or different;

$R^{43}$ represents:

hydrogen or halogen;

straight or branched chain alkyl having from 1 to 12 carbon atoms which is unsubstituted or substituted by one or more halogen atoms; or an unsubstituted amino group;

$R^{44}$ represents:

halogen;

straight or branched chain alkyl having from 1 to 12 carbon atoms which is unsubstituted or substituted by one or more halogen atoms;

straight or branched chain alkylsulphonyl having from 1 to 12 carbon atoms which is unsubstituted or substituted by one or more halogen atoms;

or sulphamoyl.

10. The composition according to claim 9 in which the 2,6-dinitroaniline herbicide is pendimethalin, which is N-(1-ethylpropyl)-3,4-dimethyl-2,6-dinitrobenzenamine.

11. The composition according to claim 1 in which (b) is aclonifen.

12. The composition according to claim 1 in which (b) is diuron.

13. The composition according to claim 1 in which (b) is a hydroxybenzonitrile herbicide.

14. The composition according to claim 13 in which the hydroxybenzonitrile herbicide is bromoxynil or ioxynil in the form of the parent phenol or an agriculturally acceptable salt or ester thereof, or a mixture thereof.

15. A method of controlling the growth of weeds at a locus which comprises applying to said locus a synergistic herbicidally effective amount of:

(a) 2-cyano-3-cyclopropyl-1-(2-methylsulphonyl-4-trifluoromethylphenyl)propan-1,3-dione, or an agriculturally acceptable salt, metal complex or enolic tautomeric form thereof; and (b) at least one member selected from the group consisting of a triazine herbicide, a chloroacetamide herbicide, a 2,6-dinitroaniline herbicide, aclonifen, which is 2-chloro-6-nitro-3-phenoxyaniline; diuron, which is 3-(3,4-dichlorophenyl)-1,1-dimethylurea; and a hydroxybenzonitrile herbicide.

16. The method according to claim 15 in which the locus is an area used, or to be used for growing a crop.

17. The method according to claim 16 in which the crop is maize or sugarcane.

18. The method according to claim 15 in which (b) is a triazine herbicide.

19. The method according to claim 18 in which the triazine herbicide is a compound of formula II:

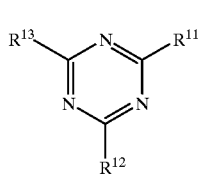

(II)

wherein $R^{11}$ represents chlorine or straight- or branched chain alkylthio or alkoxy having from one to six carbon atoms; $R^{12}$ represents azido, monoalkylamino, dialkylamino or cycloalkylamino, in which the alkyl or cycloalkyl moieties are optionally substituted by one or more substituents selected from the group consisting of cyano and alkoxy; and $R^{13}$ represents straight- or branched-chain N-alkylamino having from one to six carbon atoms;

or of formula IIa:

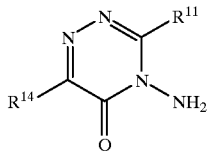

wherein $R^{14}$ represents straight- or branched chain alkyl having from one to six carbon atoms.

20. The method according to claim 19 in which the triazine herbicide is atrazine, which is (6-chloro-$N^2$-ethyl-$N^6$-isopropyl-1,3,5-triazine-2,4-diamine), or metribuzin, which is (4-amino-6-tert-butyl-3-methylthio-1,2,4-triazin-5 (4H)-one).

21. The method according to claim 20 in which from 5 g to 500 g of (a) and from 250 g to 5000 g of (b) are applied per hectare.

22. The method according to claim 21 in which from 25 g to 200 g of (a) and from 500 g to 1500 g of (b) are applied per hectare.

23. The method according to claim 19 in which from 5 g to 500 g of (a) and from 250 g to 5000 g of (b) are applied per hectare.

24. The method according to claim 23 in which from 25 g to 200 g of (a) and from 500 g to 1500 g of (b) are applied per hectare.

25. The method according to claim 18 in which from 5 g to 500 g of (a) and from 250 g to 5000 g of (b) are applied per hectare.

26. The method according to claim 25 in which from 25 g to 200 g of (a) and from 500 g to 1500 g of (b) are applied per hectare.

27. The method according to claim 25 in which the triazine herbicide is ametryn and from 250 g to 4000 g thereof are applied per hectare.

28. The method according to claim 27 in which the amount of ametryn applied is from 500 g to 2000 g per hectare.

29. The method according to claim 16 in which (b) is a chloroacetamide herbicide.

30. The method according to claim 29 in which the chloroacetamide herbicide is of formula (III)

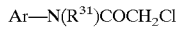

wherein
$R^{31}$ represents hydrogen, $C_{1-6}$ alkyl, haloalkyl, alkoxy or alkoxyalkyl; alkenyl, haloalkenyl, alkynyl, haloalkynyl or acylamidoalkyl having up to six carbon atoms; and Ar represent thienyl or phenyl optionally substituted by one or more members selected from the group consisting of halogen, amino, $C_{1-6}$ alkyl, haloalkyl, alkoxy and alkoxyalkyl.

31. The method according to claim 30 in which the chloroacetamide herbicide is acetochlor, which is 2-chloro-N-ethoxymethyl-6'-ethylacet-o-toluidide; or metolachlor, which is 2-chloro-6'-ethyl-N-(2-methoxy-1-methylethyl) acet-o-toluidide or an isomeric mixture thereof.

32. The method according to claim 31 in which from 0.5 g to 512 g of (a) and from 8 g to 4000 g of (b) are applied per hectare.

33. The method according to claim 32 in which from 25 g to 150 g of (a) and from 350 g to 2000 g of (b) are applied per hectare.

34. The method according to claim 30 in which from 0.5 g to 512 g of (a) and from 8 g to 4000 g of (b) are applied per hectare.

35. The method according to claim 34 in which from 25 g to 150 g of (a) and from 350 g to 2000 g of (b) are applied per hectare.

36. The method according to claim 29 in which from 0.5 g to 512 g of (a) and from 8 g to 4000 g of (b) are applied per hectare.

37. The method according to claim 36 in which from 25 g to 150 g of (a) and from 350 g to 2000 g of (b) are applied per hectare.

38. The method according to claim 16 in which (b) is a 2,6-dinitroaniline herbicide.

39. The method according to claim 38 in which the 2,6-dinitroaniline herbicide is a compound of the formula IV:

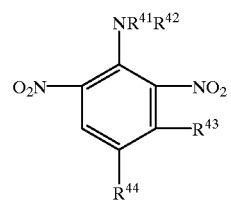

wherein:
$R^{41}$ represents:
straight or branched chain alkyl or alkenyl having up to 12 carbon atoms which is unsubstituted or substituted by one or more halogen atoms or cycloalkyl groups;
$R^{42}$ represents hydrogen or a group $R^{41}$ as defined above, $R^{41}$ and $R^{42}$ being the same or different;

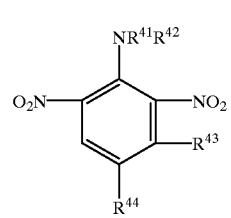

$R^{43}$ represents:
hydrogen or halogen;
straight or branched chain alkyl having from 1 to 12 carbon atoms which is unsubstituted or substituted by one or more halogen atoms; or
an unsubstituted amino group;
$R^{44}$ represents:
halogen;
straight or branched chain alkyl having from 1 to 12 carbon atoms which is unsubstituted or substituted by one or more halogen atoms;
straight or branched chain alkylsulphonyl having from 1 to 12 carbon atoms which is unsubstituted or substituted by one or more halogen atoms;
or sulphamoyl.

40. The method according to claim 39 in which the 2,6-dinitroaniline herbicide is pendimethalin, which is N-(1-ethylpropyl)-3,4-dimethyl-2,6-dinitrobenzenamine.

41. The method according to claim 40 in which from 0.5 g to 512 g of (a) and from 8 g to 3000 g of (b) are applied per hectare.

42. The method according to claim 41 in which from 20 g to 200 g of (a) and from 150 g to 2000 g of (b) are applied per hectare.

43. The method according to claim 42 in which from 25 g to 150 g of (a) and from 250 g to 1000 g of (b) are applied per hectare.

44. The method according to claim 39 in which from 0.5 g to 512 g of (a) and from 8 g to 3000 g of (b) are applied per hectare.

45. The method according to claim 44 in which from 20 g to 200 g of (a) and from 150 g to 2000 g of (b) are applied per hectare.

46. The method according to claim 45 in which from 25 g to 150 g of (a) and from 250 g to 1000 g of (b) are applied per hectare.

47. The method according to claim 38 in which from 0.5 g to 512 g of (a) and from 8 g to 3000 g of (b) are applied per hectare.

48. The method according to claim 47 in which from 20 g to 200 g of (a) and from 150 g to 2000 g of (b) are applied per hectare.

49. The method according to claim 48 in which from 25 g to 150 g of (a) and from 250 g to 1000 g of (b) are applied per hectare.

50. The method according to claim 16 in which (b) is aclonifen.

51. The method according to claim 50 in which from 1 g to 500 g of (a) and from 30 g to 2500 g of (b) are applied per hectare.

52. The method according to claim 51 in which from 10 g to 200 g of (a) and from 500 g to 1000 g of (b) are applied per hectare.

53. The method according to claim 16 in which (b) is diuron.

54. The method according to claim 53 in which from 0.5 g to 500 g of (a) and from 100 g to 3000 g of (b) are applied per hectare.

55. The method according to claim 54 in which from 25 g to 150 g of (a) and from 500 g to 2000 g of (b) are applied per hectare.

56. The method according to claim 16 in which (b) is a hydroxybenzonitrile herbicide.

57. The method according to claim 56 in which the hydroxybenzonitrile herbicide is bromoxynil or ioxynil in the form of the parent phenol or an agriculturally acceptable salt or ester thereof, or a mixture thereof.

58. The method according to claim 57 in which from 5 g to 500 g of (a) and from 30 g to 600 g acid equivalent of (b) are applied per hectare.

59. The method according to claim 58 in which from 20 g to 300 g of (a) and from 60 g to 200 g acid equivalent of (b) are applied per hectare.

60. The method according to claim 56 in which from 5 g to 500 g of (a) and from 30 g to 600 g acid equivalent of (b) are applied per hectare.

61. The method according to claim 60 in which from 20 g to 300 g of (a) and from 60 g to 200 g acid equivalent of (b) are applied per hectare.

* * * * *